United States Patent [19]

Ninomiya et al.

[11] Patent Number: 5,105,029

[45] Date of Patent: Apr. 14, 1992

[54] PROCESS FOR RECOVERING A LOWER ALCOHOL FROM A CATECHOL-LOWER ALCOHOL REACTION PRODUCT SOLUTION

[75] Inventors: Kohei Ninomiya; Kanji Nakagawa, both of Ichihara; Yoichi Nishida, Ube, all of Japan

[73] Assignee: Ube Industries, Inc., Ube, Japan

[21] Appl. No.: 724,934

[22] Filed: Jul. 2, 1991

[30] Foreign Application Priority Data

Jul. 3, 1990 [JP] Japan .................................. 2-174594

[51] Int. Cl.⁵ ...................... C07C 27/26; C07C 29/74; C07C 37/68
[52] U.S. Cl. .................................... 568/872; 568/747; 568/804; 568/854; 568/868; 568/870
[58] Field of Search ............... 568/804, 810, 747, 854, 568/868, 870, 872

[56] References Cited

U.S. PATENT DOCUMENTS

| 3,398,061 | 8/1968 | Taul | 568/872 |
| 4,062,900 | 12/1977 | Tanabe et al. | 568/872 |

FOREIGN PATENT DOCUMENTS 2538381 6/1984 France .................................. 568/872

7405513 10/1974 Netherlands .................................. 568/872

Primary Examiner—Werren B. Lone
Attorney, Agent, or Firm—Finnegan, Henderson, Farabow, Garrett & Dunner

[57] ABSTRACT

A lower alcohol, for example, ethyl alcohol, is recovered from a reaction mixture resulted from a reaction of catechol with a lower alcohol in such a manner that the reaction mixture is distilled and separated into a distilled light vapor fraction comprising non-reacted lower alcohol and water and a residual fraction comprising a reaction product and non-reacted catechol; the distilled light vapor fraction is further distilled and separated into a distilled vapor fraction comprising the lower alcohol in an increased concentration and a residual water fraction; the distilled vapor fraction is fed to a gas-separating membrane module which allows water vapor to selectively permeate therethrough, and separated into a non-permeated fraction which comprises the lower alcohol in a high concentration, which is left in the feed side of the membrane, and a permeated fraction which comprises water in a high concentration, which is returned from the delivery side of the membrane to the further distilling step, and the non-permeated fraction is cooled and recovered.

6 Claims, 2 Drawing Sheets

PROCESS FOR RECOVERING A LOWER ALCOHOL FROM A CATECHOL-LOWER ALCOHOL REACTION PRODUCT SOLUTION

BACKGROUND OF THE INVENTION

1) Field of the Invention

The present invention relates to a process for recovering a lower alcohol from a reaction mixture containing a reaction product of catechol with the lower alcohol. More particularly, the present invention relates to a process for recovering a lower alcohol from a reaction mixture containing (i) a reaction product of catechol with a lower alcohol, (ii) a by-product consisting of water, and (iii) non-reacted catechol and lower alcohol, by separating the liquid reaction mixture into (a) a vapor fraction comprising the non-reacted lower alcohol and water and (b) another fraction comprising the reaction product and the non-reacted catechol, in a first distillation step; and by recovering the non-reacted lower alcohol from the vapor fraction in a second distillation step and then in a gas-separating step, using a gas-separating membrane which allows a selective permeation of vapor therethrough.

2) Description of the Related Art

It is known that catechol reacts with a lower alcohol to produce an o-lower alkoxy phenol or lower alkyl catechol in accordance with the following reaction:

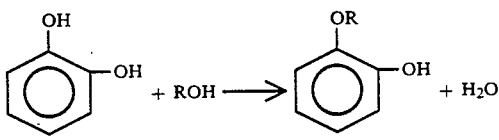

wherein R represents an alkyl radical.

The o-lower alkoxy phenol, for example, guaiacol (o-methoxyphenol or methylcatechol) or guethol (o-ethoxyphenol or ethylcatechol), is useful as a material for producing vanillin or ethylvanillin of the formula:

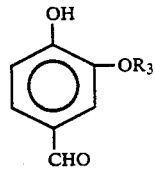

Guaiacol is produced by a reaction of catechol with methyl alcohol, and guethol is produced from a reaction of catechol with ethyl alcohol.

The resultant reaction mixture contains (i) a reaction product of catechol with the lower alcohol, (ii) a by-product consisting of water, and (iii) non-reacted catechol and lower alcohol.

In a conventional process, the collection of the reaction product and the recovery of the non-reacted lower alcohol from the reaction mixture are carried out by using a distillation system in which a plurality of distillation columns are combined in series, as shown in, for example, FIG. 2.

In this conventional process, a liquid reaction mixture comprising (i) a reaction product of catechol with a lower alcohol, (ii) a by-product consisting of water and (iii) the non-reacted catechol and lower alcohol is subjected to a first distillation step to separate a resultant vapor fraction comprising the non-reacted lower alcohol and water from a remaining fraction comprising the reaction product and the non-reacted catechol, which respectively have a higher boiling point than that of the lower alcohol and water, and then the vapor fraction comprising the lower alcohol and water is subjected to a plurality of distillation steps to separate the lower alcohol from water. In those distillation steps, a very large amount of heat energy (for example, steam) must be consumed to separate each of the above-mentioned compounds in the reaction mixture, while maintaining a reflux ratio at a high level in each distillation column.

Also, since the lower alcohol and water forms an azeotropic mixture, it is very difficult to recover the lower alcohol in a high concentration from the azeotropic mixture thereof.

Namely, to recover the lower alcohol in a high concentration from the lower alcohol-water mixture by a distillation method, an azeotropic agent consisting of, for example, benzene for the lower alcohol must be added to the lower alcohol-water mixture to selectively remove water from the mixture, but the use of the azeotropic agent, for example, benzene, results in a raise in the cost and a complicated operation of the recovering step. Also, it is necessary to remove the azeotropic agent from the recovered lower alcohol.

SUMMARY OF THE INVENTION

An object of the present invention is to provide a process for recovering a lower alcohol from a reaction mixture resulted from a reaction of catechol with a lower alcohol, with a reduced energy consumption.

Another object of the present invention is to provide a process for recovering a lower alcohol in a high concentration from a reaction mixture resulted from a reaction of catechol with a lower alcohol, without using an azeotropic agent for the lower alcohol.

The above-mentioned objects can be attained by the process of the present invention for recovering a lower alcohol from a reaction mixture resulted from a reaction of catechol with a lower alcohol, comprising the steps of:

(A) first distilling a liquid reaction mixture comprising a reaction product of catechol with a lower alcohol, a by-product consisting of water, and non-reacted catechol and lower alcohol by a first distillation column, to collect a resultant light vapor fraction comprising the non-reacted lower alcohol and water through a top outlet of the first distillation column, while recovering a resultant residual fraction comprising the reaction product and the non-reacted catechol through a bottom outlet of the first distillation column;

(B) second distilling the collected light vapor fraction by a second distillation column, to collect a resultant vapor fraction containing the non-reacted lower alcohol in an increased concentration through a top outlet of the second distillation column, while discharging a resultant residual fraction comprising water in an increased concentration through a bottom outlet of the second distillation column;

(C) feeding the collected vapor fraction into a gas-separating module comprising therein at least one gas-separating membrane which allows a selective permeation of water vapor therethrough, to recover a resultant non-permeated vapor fraction containing the non-reacted lower alcohol in a further increased concentration, from a feed side of the gas-separating membrane, while discharging a resultant permeated vapor fraction containing water in an increased concentration, from a delivery side of the gas-separating membrane;

(D) cooling the recovered, non-permeated vapor fraction to recover the resultant liquid fraction containing the concentrated lower alcohol; and (E) returning the permeated vapor fraction from the delivery side of the gas-separating membrane into the second distillation column.

DESCRIPTION OF THE PREFERRED EMBODIMENTS

In the process of the present invention, a lower alcohol is recovered from a reaction mixture derived from a reaction of catechol with a lower alcohol.

The lower alcohol is selected from those having 1 to 4 carbon atoms, for example, methyl alcohol, ethyl alcohol, propyl alcohol and butyl alcohol.

Usually, the reaction of catechol with a lower alcohol is carried out in a gas phase in the presence of a catalyst, for example, acid catalyst, and the resultant reaction mixture is collected usually in the state of a liquid.

The reaction mixture usually comprises a reaction product of catechol with a lower alcohol, for example, guaiacol or guethol in an amount of 10 to 40% by weight, preferably, 20 to 30% by weight, a by-product consisting of water in an amount of 1 to 10% by weight, preferably 2 to 6% by weight, non-reacted catechol in an amount of 20 to 50% by weight, preferably 30 to 40% by weight and non-reacted lower alcohol in an amount of 20 to 60% by weight, preferably 30 to 40% by weight.

In the process of the present invention, a lower alcohol is recovered from the reaction mixture by a first distilling step (A) in which a vapor fraction containing the lower alcohol and water is collected, a second distilling step (B) in which the lower alcohol in the vapor fraction is concentrated, a gas-separating step (C) in which a water-concentrated vapor fraction is allowed to selectively permeate through a gas-separating membrane to a delivery side of the membrane whereas a lower alcohol-concentrated vapor fraction is left in a feed side of the membrane, and thus the lower alcohol-enriched fraction is separated from the water-concentrated fraction, a cooling step (D) in which the lower alcohol-concentrated fraction is liquefied and recovered, and a returning step (E) in which the permeated fraction in the gas-separating step (C) is returned to the second distilling step (B).

Figure 1:
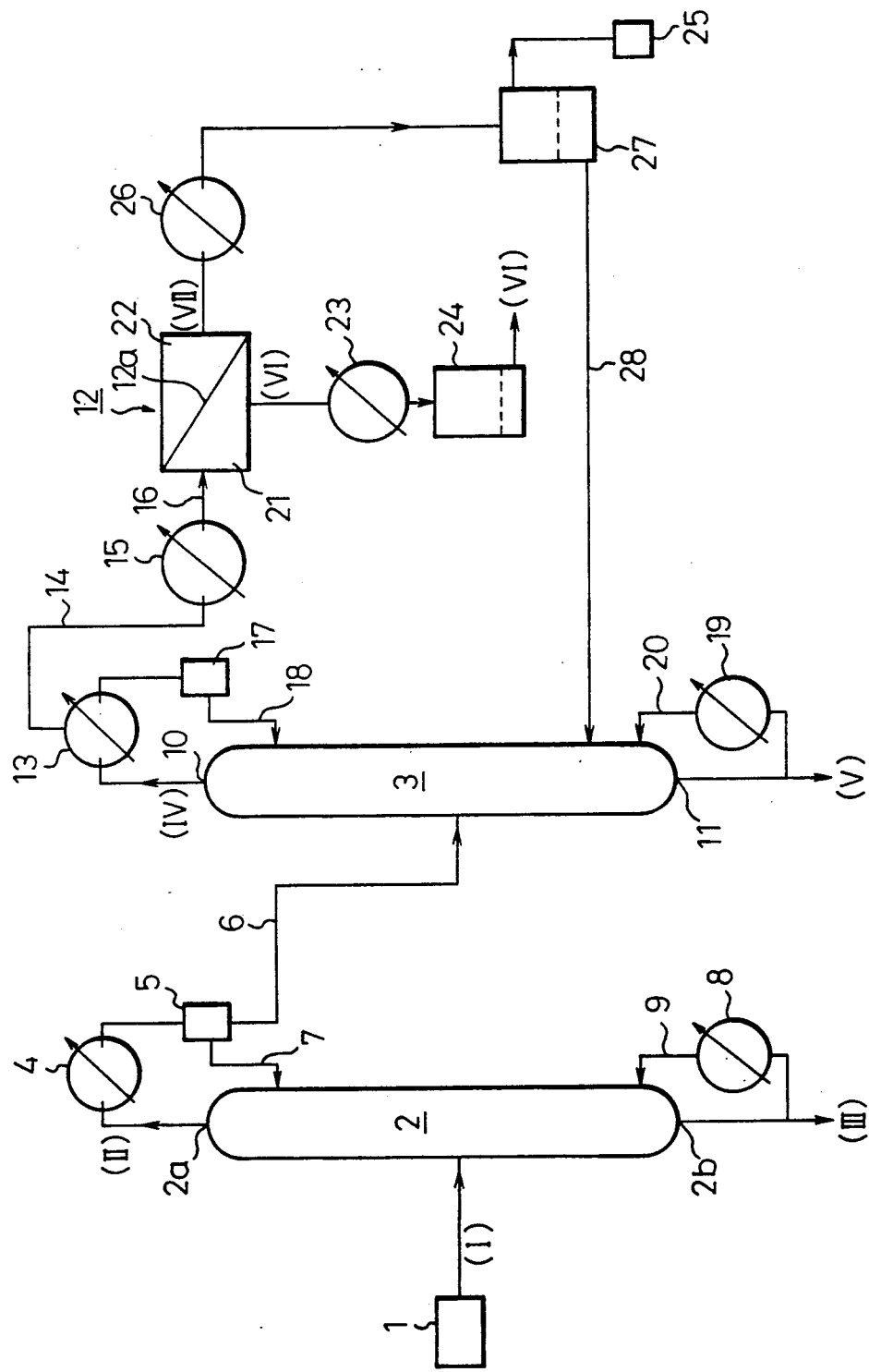
FIG. 1 is a flow sheet of an embodiment of the process of the present invention for recovering a lower alcohol from a reaction mixture resulted from a reaction of catechol with a lower alcohol; and, FIG. 2 is a flow sheet of a conventional process for recovering the lower alcohol from the above-mentioned reaction mixture.

Referring to FIG. 1 showing the flow of the process of the present invention, a reaction mixture (I) is supplied from a reaction mixture-supply source 1 into a middle portion of a first distillation column 2 and first distilled at a predetermined distilling temperature, for example, a temperature of 220° C. to 270° C. in a bottom portion and a temperature of 70° C. to 100° C. in a top portion of the first distillation column 2 under a predetermined pressure, for example, 0.1 to 1.0 kg/cm$^2$G, preferably 0.5 to 0.6 kg/cm$^2$G.

As a result of the first distilling step, a distilled light vapor fraction (II) containing the non-reacted lower alcohol and water is discharged from the first distillation column 2 through a top outlet 2a thereof and a residual fraction (III) comprising the reaction product and the non-reacted catechol is recovered from the first distillation column 2 through a bottom outlet 2b thereof.

The distilled light fraction (II) is introduced into a middle portion of a second distillation column 3 through a cooler 4 in which the vapor fraction (II) is liquefied, a receiver tank 5, and a conduit 6. A portion of the distilled light fraction (II) is returned from the receiver tank 5 to the first distillation column 2 through a conduit 7. Also, a portion of the residual fraction (III) withdrawn through the bottom outlet 3 is returned to the first distillation column 2 through a heater 8 and a conduit 9.

The light fraction (II) introduced in the second distillation column 3 is again distilled therein at a predetermined distilling temperature; for example, a bottom temperature of 120° C. to 140° C. and a top temperature of 90° C. to 110° C., under a predetermined pressure of 1.4 to 2.5 kg/cm$^2$G, preferably 1.5 to 1.7 kg/cm$^2$G.

As a result of the second distilling step, a distilled vapor fraction (IV) comprising the non-reacted lower alcohol in an increased concentration is discharged from the second distillation column 3 through a top outlet 10, and a residual fraction (V) comprising water in an increased concentration is discharged from the second distillation column 3 through a bottom outlet 11. Preferably, the fraction (V) consists essentially of water.

The operational conditions of the first and second distilling steps, for example, the temperatures of the feed, the temperatures in the top and bottom portions of the distillation column, the pressure in the top portion and reflux ratio, can be varied in consideration of the type, composition and amount of the feed.

The distilled vapor fraction (IV) is fed into a gas-separating membrane module 12 having at least one gas-separating membrane 12a through a cooler 13, a conduit 14, a super heater 15 and a conduit 16.

A portion of the residual fraction (V) recovered through the bottom outlet 11 of the second distillation column 3 is returned to the second distillation column 3 through a heater 19 and a conduit 20.

The distilled vapor fraction (IV) discharged from the second distillation column (3) is cooled in a cooler 13 in which a portion of the distilled vapor fraction (IV) is liquefied.

The remaining portion of the distilled vapor fraction (IV) is discharged through a top outlet of the cooler 13 and heated in the super heater 15 at a temperature of, for example, 110° C. to 130° C. for an ethyl alcohol-containing fraction. The super heated vapor fraction containing the non-reacted lower alcohol in an increased concentration is fed to a feed side 21 of the gas-separating membrane 12a in the module 12. Optionally, the distilled vapor fraction (IV) is directly fed to the gas-separating membrane module 12.

Preferably, the distilled vapor fraction (IV) fed to the gas-separating membrane module 12 comprises 80 to 98% by weight, more preferably 90 to 95%, of the non-reacted lower alcohol, and 2 to 20%, more preferably 5 to 10% by weight of water.

The gas-separating membrane 12a allows water vapor to selectively permeate therethrough, and thus can separate the vapor fraction (IV) into a non-permeated vapor fraction (VI) which is left in the fed side 21 of the gas-separating membrane 12a and a permeated vapor fraction (VII) which reaches a delivery side 22 of the gas-separating membrane 12a.

The non-permeated fraction (VI) contains the non-reacted lower alcohol in a further increased concentration, for example, 95% to 99.9% by weight.

The non-permeated fraction (VI) is collected from the feed side 21 of gas-separating membrane 12a and cooled by a cooler 23. The resultant liquefied fraction (VI) is received in a tank 24. The liquefied fraction (VI) preferably comprises 95 to 99.9%, more preferably 98 to 99.5% by weight of the non-reacted lower alcohol and 0.1 to 5%, more preferably 0.5 to 2% by weight of water.

The delivery side 22 of the gas-separating membrane 12a in the module 12 is preferably connected to a pressure-reducing apparatus or a vacuum pump 25 through a cooler 26, and a receiving tank 27 to maintain the delivery side 22 under a reduced pressure, for example, 10 to 500 Torr, preferably 20 to 300 Torr.

The permeated vapor fraction (VII) is cooled by the cooler 26 to liquefy the permeated fraction (VII). The liquefied fraction (VII) contains 10 to 70% by weight of the lower alcohol and 90 to 30% by weight of water. The liquefied fraction (VII) is received in the tank 27, and then returned to a lower portion of the second distillation column 3 through a conduit 28.

The gas-separating membrane usable for the present invention is not restricted to those of a specific type and size, but preferably, the gas-separating membrane allows water vapor to permeate therethrough at a water vapor permeation rate ($P_{H_2O}$) of $0.1 \times 10^{-3}$ to $5.0 \times 10^{-3}$ Ncm$^3$/cm$^2$.sec.cmHg, more preferably $0.3 \times 10^{-3}$ to $3.0 \times 10^{-3}$ Ncm$^3$/cm$^2$.sec.cmHg at 100° C., and a ratio ($P_{H_2O}/P_{EtOH}$) of a water vapor permeation rate ($P_{H_2O}$) to an ethyl alcohol vapor permeation rate, ($P_{EtOH}$) of 80 to 800, more preferably 100 to 500. The unit "Ncm$^3$" refers to a volume in cm$^3$ at a standard temperature (0° C.) and under a standard pressure (1 atmosphere).

The gas-separating membrane usable for the process of the present invention preferably comprises a polymeric material having a satisfactory heat resistance and water resistance, for example, an aromatic polysulfon resin, aromatic polyamide resin and aromatic polyimide resin.

More preferably, the gas-separating membrane is an asymmetric membrane comprising a very thin dense layer and a thick porous layer. The dense layer serves as an active layer and the porous layer supports the active layer thereon.

Figure 2:
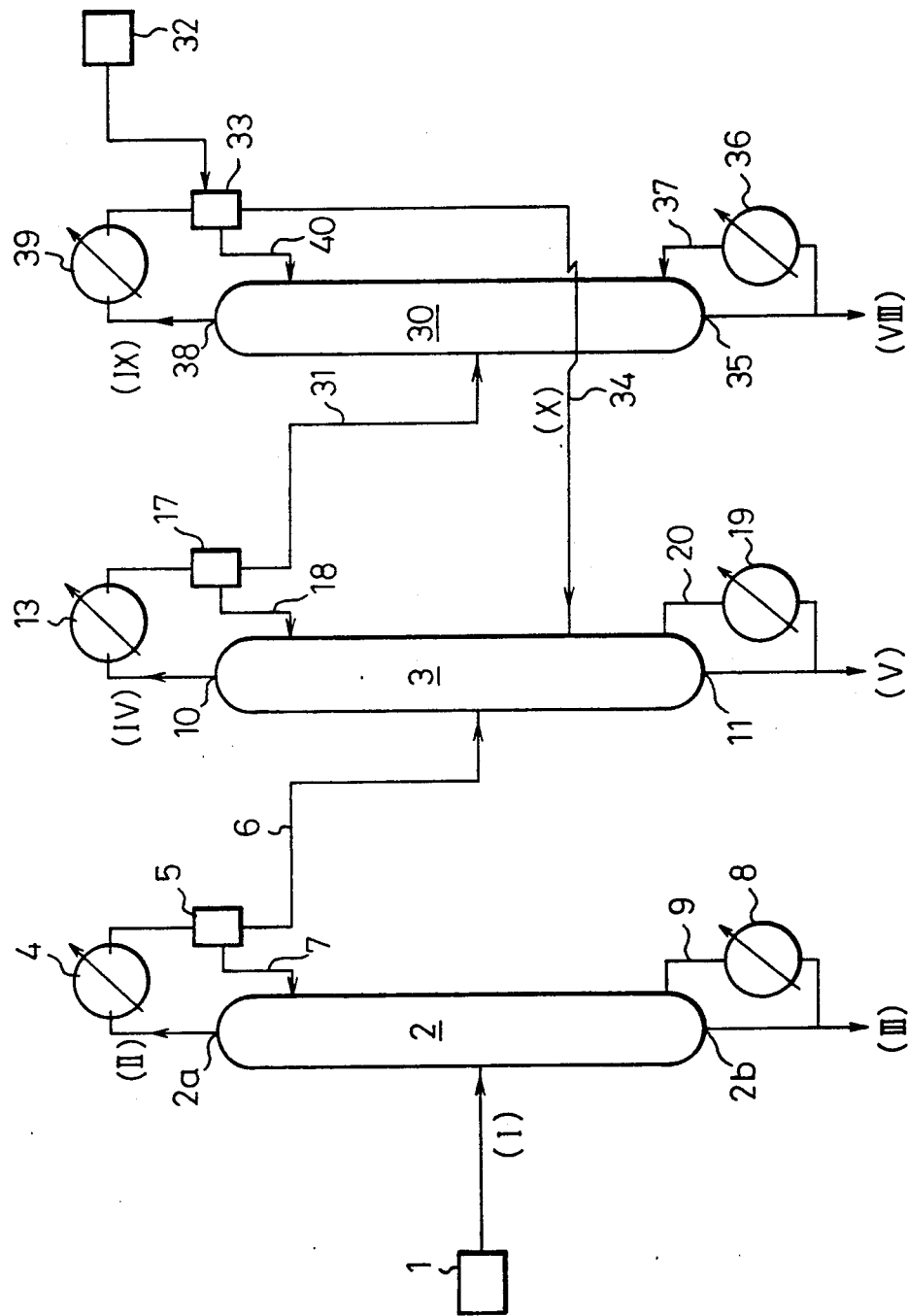

In a conventional distillation system as shown in FIG. 2, the same first and second distillation column 2 and 3 are combined with a third distillation column 30.

The distilled vapor fraction (IV) discharged from the second distillation column 3 is cooled by a cooler 13, and the cooled fraction (IV) is received in a tank 17 and then introduced into a middle portion of the third distillation column 30 through a conduit 31. A portion of the cooled fraction (IV) is returned from the tank 17 to the second distillation column 3 through a conduit 18.

An azeotropic agent, for example, benzene is supplied from an azeotropic agent-supply source 32 to a middle portion of the second distillation column 3 through a tank 33 and a conduit 34. The azeotropic agent effectively promotes the separation of water from the lower alcohol in the distillation.

The fraction (IV) is distilled by the third distillation column 30 at a top temperature of 50° C. to 70° C., at a bottom temperature of 70° C. to 100° C. under a pressure of 0.0 to 0.5 kg/cm$^2$G.

A residual (non-distilled) fraction (VIII) is discharged from the third distillation column 30 through a bottom outlet 35. The residual fraction (VIII) comprising the lower alcohol in an increased concentration of 96 to 99.9% by weight is recovered.

A portion of the discharged residual fraction (VIII) is heated in a heater 36 and then returned to a bottom portion of the third distillation column 30 through a conduit 37.

Also, the resultant distilled vapor fraction (IX) is discharged from the third distillation column 30 through a top outlet 38. The fraction (IX) contains water and the azeotropic agent in increased concentrations. This fraction (IX) is cooled by a cooler 39 and received by a tank 33. A portion of the fraction (IX) in the tank 33 is returned into an upper portion of the third distillation column 30 through a tank 33 and a conduit 40. A portion (X) of the cooled fraction (IX) in the tank 33 is withdrawn through the bottom of the tank 33 and is returned to the second distillation column 3 through a conduit 34.

EXAMPLES

The present invention will be further explained by the following examples.

EXAMPLE 1

A reaction mixture in an amount of 979 kg/h was prepared by a continuous reaction of 547 kg/h of catechol with 431 kg/h of ethyl alcohol.

This reaction mixture contained guethol (reaction product), non-reacted catechol, non-reacted ethyl alcohol and water (by-product), in the amounts as shown in Table 1.

The reaction mixture was subjected to a process for recovering the non-reacted ethyl alcohol by using the recovering apparatus as shown in FIG. 1.

Referring to FIG. 1, the first distillation column 2 had a temperature of 89° C. in the top portion and a temperature of 248° C. in the bottom portion of the column 2, and a pressure of 0.5 kg/cm$^2$G.

The distilled light vapor fraction (II) comprising ethyl alcohol and water in the amounts shown in Table 1 was introduced to a middle portion of the second distillation column 3.

The residual fraction (III) comprising guethol and the non-reacted catechol in the amounts shown in Table 1 was recovered.

The second distillation column 3 had a top temperature of 100° C., a bottom temperature of 125° C. and a pressure of 1.5 kg/cm$^2$G.

The distilled vapor fraction (IV) comprised ethyl alcohol in the increased concentration and water in the decreased concentration as shown in Table 1.

The residual fraction (V) consisted essentially of water as indicated in Table 1.

The vapor fraction (IV) was heated at a temperature of 120° C. by a super heater 15 and then introduced into the gas-separating membrane module 12 containing therein a number of asymmetric gas-separating membranes made of an aromatic polyimide resin.

The feed side 21 of the membrane 12a had a pressure of 1.5 kg/cm$^2$G and the delivery side 22 of the membrane 12a had a reduced pressure of 100 Torr.

The gas-separating membranes 12a had a water vapor permeation rate ($P_{H_2O}$) of $1.0 \times 10^{-3}$ Ncm$^3$/cm$^2$.sec.cmHg and a ethyl alcohol vapor permeation rate ($P_{EtOH}$) of $3 \times 10^{-6}$ Ncm$^3$/cm$^2$.sec.cmHg.

The permeation rate ratio ($P_{H_2O}/P_{EtOH}$) was about 300. The gas-separating membranes could be practically used at a temperature of from 10° C. to 180° C.

The non-permeated fraction (VI) collected at the feed side 21 of the membranes 12a comprised the non-reacted ethyl alcohol in the very high concentration of 99.3% by weight and water in the very small amount of 0.7% by weight.

The permeated fraction (VII) recovered at the delivery side 22 of the membranes 12a contained water in the increased amount as indicated in Table 1.

The total energy consumed in the heating procedures in the second distillation column 3 and the gas-separating membrane module 12 was 202 mega calories/h.

TABLE 1

| Item Fraction | Flow rate (kg/hr) | Guethol | Non-reacted catechol | Non-reacted ethyl alcohol | Water |
|---|---|---|---|---|---|
| Reaction mixture (I) | 979 | 26.6 | 34.7 | 34.8 | 3.9 |
| Portion of fraction (II) introduced into second column 3 | 379 | — | — | 90.0 | 10.0 |
| Residual fraction (III) | 600 | 43.3 | 56.7 | — | — |
| Portion of vapor fraction (IV) introduced into gas-separating module 12 | 386 | — | — | 93.6 | 6.4 |
| Residual fraction (V) | 35 | — | — | — | 100.0 |
| Non-permeated fraction (VI) | 344 | — | — | 99.3 | 0.7 |
| Permeated fraction (VII) | 42 | — | — | 46.5 | 53.5 |

COMPARATIVE EXAMPLE 1

The same procedures as in Example 1 were carried out except that the apparatus shown in FIG. 2 was used in place of the apparatus of FIG. 1.

In this apparatus, an azeotropic agent consisting of benzene was used in a small amount in the second and third distillation columns 3 and 30.

The third distillation column 30 had a top temperature of 64° C., a bottom temperature of 80° C., and a pressure of 0.0 kg/cm$^2$G.

The vapor fraction (IV) collected through the top outlet 10 of the second distillation column 3, and the residual fraction (VIII) collected through the bottom outlet 35 and the vapor fraction (IX) collected through the top outlet 38 of the third distillation had the compositions as indicated in Table 2.

TABLE 2

| Item Fraction | Flow rate (kg/hr) | Guethol | Non-reacted catechol | Non-reacted ethyl alcohol | Water | Benzene |
|---|---|---|---|---|---|---|
| Reaction mixture (I) | 979 | 26.6 | 34.7 | 34.8 | 3.9 | — |
| Portion of fraction (II) introduced into second column 3 | 372 | — | — | 90.0 | 10.0 | — |
| Residual fraction (III) | 600 | 43.3 | 56.7 | — | — | — |
| Portion of fraction (IV) introduced into third column 30 | 372 | — | — | 94.7 | 4.7 | 0.6 |
| Residual fraction (V) | 35 | — | — | — | 100.0 | — |
| Retured portion (X) | 27 | — | — | 40.0 | 52.2 | 7.8 |
| Residual fraction (VIII) | 344 | — | — | 99.0 | 1.0 | — |

In the second and third distillation columns 3 and 30, the total energy consumed by the heaters was 439 mega calories/hr.

In view of Example 1 and Comparative Example 1, it is clear that the gas-separating step of the process of the present invention is effective for recovering the non-reacted lower alcohol in a satisfactory concentration. Also, the energy consumption in the gas-separating step is lower than that of the conventional process.

We claim:

1. A process for recovering a lower alcohol from a reaction mixture resulted from a reaction of catechol with a lower alcohol; comprising the steps of:

(A) distilling a reaction mixture comprising a reaction product of catechol with a lower alcohol, a by-product consisting of water and non-reacted catechol and lower alcohol by a first distillation column, to collect a resultant light vapor fraction comprising the non-reacted lower alcohol and water through a top outlet of the first distillation column, while recovering a resultant residual fraction comprising the reaction product and the non-reacted catechol through a bottom outlet of the first distillation column;

(B) distilling the collected light vapor fraction by a second distillation column, to collect a resultant vapor fraction comprising the non-reacted lower alcohol in an increased concentration through a top outlet of the second distillation column, while discharging a resultant residual fraction comprising water in an increased concentration through a bottom outlet of the second distillation column;

(C) feeding the collected vapor fraction into a gas-separating module comprising therein at least one gas-separating membrane which allows a selective permeation of water vapor therethrough, to recover a resultant non-permeated vapor fraction comprising the non-reacted lower alcohol in a further increased concentration, from a feed side of the gas-separating membrane, while discharging a resultant permeated vapor fraction containing water in an increased concentration from a delivery side of the gas-separating membrane;

(D) cooling the recovered, non-permeated vapor fraction to recover the resultant liquid fraction containing the concentrated lower alcohol; and (E) returning the permeated vapor fraction from the delivery side of the gas-separating membrane to the second distillation column.

2. The process as claimed in claim 1, wherein the gas-separating membrane has a permeation rate of water vapor of $0.1 \times 10^{-3}$ to $5.0 \times 10^{-3}$ Ncm$^3$/cm$^2$. sec.cmHg.

3. The process as claimed in claim 1, wherein the gas-separating membrane exhibits a ratio ($P_{H_2O}/P_{EtOH}$) of a permeation rate of water vapor ($P_{H_2O}$) to a permeation rate of ethyl alcohol vapor ($P_{EtOH}$) of from 80 to 800.

4. The process as claimed in claim 1, wherein the gas-separating membrane comprises a member selected from the group consisting of aromatic polysulfon resins, aromatic polyamide resins and aromatic polyimide resins.

5. The process as claimed in claim 1, wherein the gas-separating membrane is an asymmetric membrane having a dense layer and a porous layer.

6. The process as claimed in claim 1, wherein the delivery side of the gas-separating membrane is under a reduced pressure.

* * * * *

UNITED STATES PATENT AND TRADEMARK OFFICE
CERTIFICATE OF CORRECTION

PATENT NO. : 5,105,029
DATED : April 14, 1992
INVENTOR(S) : KOHEI NINOMIYA et al.

It is certified that error appears in the above-identified patent and that said Letters Patent is hereby corrected as shown below:

Claim 2, col. 9, line 17, after "vapor" insert --($P_{H_2O}$)--; also delete "$Ncm^3/cm^2.sec.cmHg$" and insert therefor --$Ncm^3/cm^2 \cdot sec \cdot cmHg$--.

Signed and Sealed this

Seventeenth Day of August, 1993

Attest:

BRUCE LEHMAN

Attesting Officer  Commissioner of Patents and Trademarks